(12) United States Patent
Dhamdhere et al.

(10) Patent No.: US 9,452,119 B2
(45) Date of Patent: Sep. 27, 2016

(54) NITRONE COMPOUNDS AND THEIR USE IN PERSONAL CARE

(71) Applicant: Dow Global Technologies LLC, Midland, MI (US)

(72) Inventors: Mrunalini S. Dhamdhere, Vernon Hills, IL (US); George D. Green, Cary, IL (US); Shao-Ching Hung, Midland, MI (US); Raymond J. Swedo, Mount Prospect, IL (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 14/819,859

(22) Filed: Aug. 6, 2015

(65) Prior Publication Data

US 2015/0335546 A1 Nov. 26, 2015

Related U.S. Application Data

(63) Continuation of application No. 14/361,719, filed as application No. PCT/US2012/063668 on Nov. 6, 2012.

(60) Provisional application No. 61/564,920, filed on Nov. 30, 2011.

(51) Int. Cl.
| | |
|---|---|
| *A01N 33/24* | (2006.01) |
| *A61K 31/15* | (2006.01) |
| *A61K 8/40* | (2006.01) |
| *A61Q 19/08* | (2006.01) |
| *C07C 291/02* | (2006.01) |

(52) U.S. Cl.
CPC ............... *A61K 8/40* (2013.01); *A61Q 19/08* (2013.01); *C07C 291/02* (2013.01); *A61K 2800/522* (2013.01)

(58) Field of Classification Search
CPC .. A61K 2800/522; A61K 8/40; A61Q 19/08; C07C 251/00
See application file for complete search history.

(56) References Cited

U.S. PATENT DOCUMENTS

2010/0168112 A1* 7/2010 Kelly ................... A61K 31/405
514/238.2

FOREIGN PATENT DOCUMENTS

WO WO 2005087214 A1 * 9/2005 ............. A61K 31/15

OTHER PUBLICATIONS

Finlayson et al, J Neurosci Nurs. 2004; 36(5).*

* cited by examiner

*Primary Examiner* — Jean Cornet
(74) *Attorney, Agent, or Firm* — Edward L. Brant (57) ABSTRACT

Provided are compounds and compositions thereof that are useful as antioxidants in personal care formulations. The compounds are of the formula I:

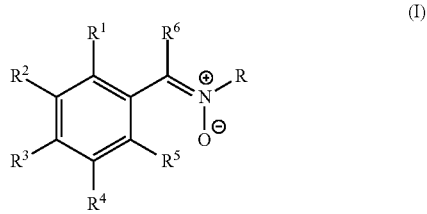

wherein R, $R^1$, $R^2$, $R^3$, $R^4$, $R^5$ and $R^6$ are as defined herein.

4 Claims, 3 Drawing Sheets

NITRONE COMPOUNDS AND THEIR USE IN PERSONAL CARE

CROSS-REFERENCE TO RELATED APPLICATIONS

This application is a continuation of nonprovisional application Ser. No. 14/361,719, filed on May 14, 2014, which claims priority from International Application No. PCT/US12/063668, filed on Nov. 6, 2012, which claims priority from provisional application Ser. No. 61/564,920, filed Nov. 30, 2011, which is incorporated herein by reference in its entirety.

FIELD

This invention relates generally to compounds and compositions that are useful as antioxidants in personal care formulations. The compounds contain both nitrone and phenolic functionalities.

BACKGROUND

Personal care compositions are important products for most consumers. Personal care compositions contain a variety of additives that provide a wide array of benefits to the composition.

Antioxidants are among the additives commonly used in personal care compositions. Antioxidants help protect the skin from the damaging effects of free radicals caused by various environmental stresses, such as exposure to UV rays. Free radicals include, for example, singlet oxygen. Free radicals cause damage to the skin with the end result being a loss of elasticity of the skin and the appearance of wrinkles leading to premature aging of the skin.

Based on the physiological mechanism of the aging process, oxidative stress due to increased level of reactive oxygen species (ROS) especially caused by physiological stress or solar ultraviolet radiation can accelerate skin aging. There is evidence that intrinsic and extrinsic aging (i.e. photoaging) have several overlapping biochemical and molecular mechanisms. Type I collagen constitutes the major structural component of dermal connective tissue and provides dermis with tensile strength and stability. Degradation of collagen in the dermis has been reported in intrinsic aged and photoaged skin. Additionally, a major signaling pathway contributing to photoaging by ROS is the up-regulation of matrix metalloproteinase-1 (MMP-1), which leads to degradation of dermal collagen, associated with aging spots and wrinkles. Therefore, stronger antioxidants are needed as potential anti-aging ingredients to provide protection.

The problem addressed by this invention is the provision of new antioxidant compositions for use in personal care, including compositions that mitigate degradation of collagen in skin.

STATEMENT OF INVENTION

We have now found that nitrone compounds of formula I, which contain nitrone and phenolic functionalities as part of the structure, are highly effective as radical scavengers and exhibit significantly better antioxidant attributes compared to previously known antioxidants for personal care applications. Moreover, the compounds have been found to inhibit radical induced degradation of collagen, thereby providing anti-aging benefits to skin.

Advantageously, it is believed that the presence of the nitrone and phenolic functionalities allows a regenerative mechanism to take place. In other words, in contrast to conventional antioxidants that are consumed sacrificially by free radicals, the nitrone antioxidants of the present invention are believed to be able to continue scavenging free radicals. This regenerative mechanism allows the nitrone antioxidants of the present invention to consume more damaging radicals than conventional antioxidants. The resulting effect of the regenerative mechanism is that the nitrone antioxidants either have equivalent efficacy at lower concentrations (as measured by duration of antioxidant protection), or higher efficacy (less oxidative damage and/or longer antioxidant protection) at equivalent concentrations as compared to conventional antioxidants. It has also been found that the performance of nitrones that have a phenolic group cannot be achieved by simply adding two different antioxidants, one with a phenolic functionality and another with nitrone functionality. Rather, the presence of both functionalities in the same molecule is an important aspect of their favorable performance.

Accordingly in one aspect, there is provided a personal care composition comprising:

(a) an antioxidant compound of formula I:

(I)

wherein R is $C_1$-$C_{10}$ alkyl, $C_3$-$C_{12}$ cycloalkyl, aryl (e.g., phenyl), or aryl-alkyl;

$R^1$, $R^2$, $R^3$, $R^4$, and $R^5$ are independently H, $C_1$-$C_{10}$ alkyl, hydroxy, $C_1$-$C_6$ alkoxy, —COOH, —COO$^-$M$^+$, or —O$^-$M$^+$, where M$^+$ is sodium, potassium, or ammonium (such as NH$_4^+$ or other protonated amine such as protonated tris (hydroxymethyl)aminomethane) ion, provided that at least one of $R^1$, $R^2$, $R^3$, $R^4$, and $R^5$ is hydroxy; and $R^6$ is H, $C_1$-$C_{10}$ alkyl, $C_3$-$C_{12}$ cycloalkyl, or phenyl; and (b) a dermatologically acceptable carrier.

In another aspect, there is provided a cosmetic method of treating skin which comprises applying to the skin a composition as described herein.

In a further aspect, new compounds are provided.

In a still further aspect, there is provided a method for inhibiting the degradation of collagen, the method comprising: topically administering to skin an effective amount of a composition as described herein.

In a yet further aspect, there is provided a method for reducing the visible signs of aging, the method comprising: applying to skin in need of such treatment a composition as described herein.

DETAILED DESCRIPTION

Unless otherwise indicated, numeric ranges, for instance as in "from 2 to 10," are inclusive of the numbers defining the range (e.g., 2 and 10).

Unless otherwise indicated, ratios, percentages, parts, and the like are by weight.

"Alkyl," as used in this specification, encompasses straight and branched chain aliphatic groups having the indicated number of carbon atoms. If no number is indicated (e.g., aryl-alkyl-), then 1-6 alkyl carbons are contemplated. Preferred alkyl groups include, without limitation, methyl, ethyl, propyl, isopropyl, butyl, isobutyl, sec-butyl, tert-butyl, pentyl, and hexyl. Unless otherwise indicated, the alkyl group is optionally substituted with 1, 2, or 3, preferably 1 or 2, more preferably 1, substituents that are compatible with the syntheses described herein. Such substituents include, but are not limited to, nitro, halogen, carboxylic acids (e.g., $C_0$-$C_6$—COOH), $C_2$-$C_6$ alkene, cyano, amido, and/or ester. Unless otherwise indicated, the foregoing substituent groups are not themselves further substituted.

The term "cycloalkyl" refers to saturated and partially unsaturated cyclic hydrocarbon groups having the indicated number of ring carbon atoms. If no number is specified, then 3 to 12 carbons, preferably 3 to 8 carbons, and more preferably 3 to 7 carbons, are contemplated. Preferred cycloalkyl groups include, without limitation, cyclopropyl, cyclobutyl, cyclopentyl, cyclopentenyl, cyclohexyl, cyclohexenyl, cycloheptyl, and cyclooctyl. Unless otherwise indicated, the cycloalkyl group is optionally substituted with 1, 2, or 3, preferably 1 or 2, more preferably 1, substituents that are compatible with the syntheses described herein. Such substituents include, but are not limited to, $C_1$-$C_6$ alkyl, nitro, halogen, carboxylic acids (e.g., $C_0$-$C_6$—COOH), $C_2$-$C_6$ alkene, cyano, amido, and/or ester. A preferred substituent is $C_1$-$C_6$ alkyl. Unless otherwise indicated, the foregoing substituent groups are not themselves further substituted.

An "aryl" group is a C6-C19 aromatic moiety comprising one to three aromatic rings. Preferably, the aryl group is a C6-C10 aryl group. Preferred aryl include, without limitation, phenyl, naphthyl, anthracenyl, and fluorenyl. More preferred are phenyl and naphthyl. Unless otherwise indicated, the aryl group is optionally substituted with 1, 2, or 3, preferably 1 or 2, more preferably 1, substituents that are compatible with the syntheses described herein. Such substituents include, but are not limited to, $C_1$-$C_6$ alkyl, nitro, halogen, carboxylic acids (e.g., $C_0$-$C_6$—COOH), $C_2$-$C_6$ alkene cyano, amido, and/or ester. Unless otherwise indicated, the foregoing substituent groups are not themselves further substituted.

As noted above, in one aspect the invention provides a composition comprising a compound of formula I and a dermatologically acceptable carrier.

In some embodiments, R in the compounds of formula I is $C_1$-$C_8$ alkyl, alternatively $C_1$-$C_6$ alkyl, or alternatively $C_1$-$C_4$ alkyl. In some embodiments, R is t-butyl, i-propyl, n-propyl, ethyl, or methyl. In some embodiments, R is 2,4,4-trimethylpentyl.

In some embodiments, R in the compounds of formula I is $C_3$-$C_{12}$ cycloalkyl, alternatively $C_4$-$C_7$ cycloalkyl. In some embodiments, R is cyclohexyl.

In some embodiments, R is aryl, preferably phenyl.

In some embodiments, R is aryl-alkyl, preferably benzyl.

In some embodiments, $R^1$ is H, OH, or $O^-M^+$.

In some embodiments, $R^4$ is H or $C_1$-$C_{10}$ alkyl (e.g., methyl).

In some embodiments, $R^5$ is H.

In some embodiments, $R^1$, $R^4$, and $R^5$ are simultaneously H.

In some embodiments, $R^3$ is OH.

In some embodiments, $R^2$ is H, $C_1$-$C_{10}$ alkyl, hydroxy, $C_1$-$C_6$ alkoxy, —COOH, or —COO$^-M^+$, where $M^+$ is sodium.

In some embodiments of the composition of the invention, the compound of formula I is as shown in Table 1:

TABLE 1

(Z)-N-(4-hydroxy-3-methoxybenzylidene)-2-methylpropan-2-amine oxide
(VAN-tBHA);

(Z)-N-(4-hydroxy-3,5-dimethylbenzylidene)cyclohexanamine oxide
DMHBz-CyHHA;

(Z)-N-(4-hydroxy-3-methoxybenzylidene)propan-2-amine oxide
VAN-IPHA;

(Z)-N-(4-hydroxy-3-methoxybenzylidene)-2,4,4-trimethylpentan-2-amine oxide
VAN-iOHA;

(Z)-N-(4-hydroxy-3-methoxybenzylidene)cyclohexanamine oxide
VAN-CyHHA;

TABLE 1-continued

(Z)-N-(4-hydroxybenzylidene)ethanamine oxide
pHBz-EHA;

(Z)-N-(4-hydroxybenzylidene)propan-1-amine oxide
pHBz-PHA;

(Z)-N-(4-hydroxybenzylidene)propan-2-amine oxide
pHBz-IPHA;

(Z)-N-(4-hydroxybenzylidene)-2-methylpropan-2-amine oxide
pHBz-tBHA;

(Z)-N-(2-hydroxybenzylidene)propan-2-amine oxide
SAL-IPHA sodium (Z)-2-hydroxy-5-((isopropyloxidoimino)methyl)benzoate
FSANa-IPHA (Z)-N-(2,4-dihydroxybenzylidene)propan-2-amine oxide
(DHBz-IPHA)

TABLE 1-continued sodium (Z)-N-(4-hydroxy-2-oxidobenzylidene)propan-2-amine oxide
(DHBzNa-IPHA)

(Z)-N-(4-hydroxy-3,5-dimethylbenzylidene)propan-2-amine oxide
(DMHBz-IPHA)

(Z)-N-(4-hydroxy-3,5-dimethylbenzylidene)-2-methylpropan-2-amine oxide
(DMHBz-tBHA)

(Z)-N-(4-hydroxy-3,5-dimethylbenzylidene)-2,4,4-trimethylpentan-2-amine oxide
(DMHBz-iOHA)

(Z)-N-(2-hydroxybenzylidene)-2-methylpropan-2-amine oxide
(SAL-tBHA)

(Z)-N-(2-hydroxybenzylidene)cyclohexanamine oxide
(SAL-CyHHA)

(Z)-N-(4-hydroxybenzylidene)aniline oxide
(pHBz-PHHA)

The following compounds of formula I are believed to be novel: (Z)—N-(4-hydroxy-3-methoxybenzylidene)-2-methylpropan-2-amine oxide; (Z)—N-(4-hydroxy-3,5-dimethylbenzylidene)cyclohexanamine oxide; (Z)—N-(4-hydroxy-3-methoxybenzylidene)propan-2-amine oxide; (Z)—N-(4-hydroxy-3-methoxybenzylidene)-2-methylpropan-2-amine oxide; (Z)—N-(4-hydroxy-3-methoxybenzylidene)-2,4,4-trimethylpentan-2-amine oxide; (Z)—N-(4-hydroxy-3-methoxybenzylidene)cyclohexanamine oxide; (Z)—N-(4-hydroxybenzylidene)ethanamine oxide; (Z)—N-(4-hydroxybenzylidene)propan-1-amine oxide; (Z)—N-(4-hydroxybenzylidene)propan-2-amine oxide; (Z)—N-(4-hydroxybenzylidene)-2-methylpropan-2-amine oxide; (Z)—N-(2-hydroxybenzylidene)propan-2-amine oxide; sodium (Z)-2-hydroxy-5-((isopropyloxidoimino)methyl)benzoate; (Z)—N-(2,4-dihydroxybenzylidene)propan-2-amine oxide; and sodium (Z)—N-(4-hydroxy-2-oxidobenzylidene)propan-2-amine oxide.

A person of ordinary skill in the art can readily determine the effective amount of the antioxidant compound of formula I that should be used in a particular composition in order to provide the benefits described herein (e.g., free radical scavenging and inhibition of collagen degradation), via a combination of general knowledge of the applicable field as well as routine experimentation where needed. By way of non-limiting example, the amount of the compound of formula I in the composition of the invention may be in the range of 0.01 to 5 weight percent based on the total weight of the composition.

Compounds of formula I may be readily prepared by those skilled in the art using known synthetic techniques. For instance, the compounds may be prepared by the reaction of a phenyl aldehyde compound (containing one or more hydroxyl groups on the phenyl, such as 4-hydroxybenzaldehyde) with an alkylhydroxylamine compound, followed by isolation and purification of the desired product.

Compositions of the invention also include a dermatologically acceptable carrier. Such material is typically characterized as a carrier or a diluent that does not cause significant irritation to the skin and does not negate the activity and properties of active agent(s) in the composition. Examples of dermatologically acceptable carriers that are useful in the invention include, without limitation, emulsions, creams, aqueous solutions, oils, ointments, pastes, gels, lotions, milks, foams, suspensions, powders, or mixtures thereof. In some embodiments, the composition contains from about 99.99 to about 50 percent by weight of the dermatologically acceptable carrier, based on the total weight of the composition.

The dermatologically acceptable carrier of the invention may also include, for instance, water, a thickener, an emollient, an emulsifier, a humectant, a surfactant, a suspending agent, a film forming agent, a foam building agent, a preservative, an antifoaming agent, a fragrance, a lower monoalcoholic polyol, a high boiling point solvent, a propellant, a colorant, a pigment, glycerin, a mineral oil, silicon feel modifiers, preservatives, emollients, or mixtures thereof.

Other additives may be included in the compositions of the invention such as, but not limited to, abrasives, absorbents, aesthetic components such as fragrances, pigments, colorings/colorants, essential oils, skin sensates, astringents, etc. (e.g., clove oil, menthol, camphor, eucalyptus oil, eugenol, menthyl lactate, witch hazel distillate), anti-caking agents, antifoaming agents, antimicrobial agents (e.g., iodopropyl butylcarbamate), other antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, skin bleaching and lightening agents (e.g., hydroquinone, kojic acid, ascorbic acid, magnesium ascorbyl phosphate, ascorbyl glucosamine), skin-conditioning agents (e.g., humectants, including miscellaneous and occlusive), skin soothing and/or healing agents (e.g., panthenol and derivatives (e.g., ethyl panthenol), aloe vera, pantothenic acid and its derivatives, allantoin, bisabolol, and dipotassium glycyrrhizinate), skin treating agents, thickeners, and vitamins (e.g., Vitamin C) and derivatives thereof.

The composition of the invention may be, for example, in the form of an oil, a gel, a solid stick, a lotion, a cream, a milk, an aerosol, a spray, a foam, a mousse, an ointment or a fatty ointment or a powder.

Compositions of the invention may be used in a variety of personal care applications, such as in cosmetics and in skin care (e.g., lotions, creams, oils, topical medicines, and sunscreens).

The compositions of the invention may be manufactured by processes well known in the art, e.g., by means of conventional mixing, dissolving, granulating, emulsifying, encapsulating, entrapping or lyophilizing processes.

As noted above, compositions of the invention, containing a compound of the formula I, are highly effective as radical scavengers. They exhibit significantly better antioxidant attributes compared to previously known antioxidants for personal care applications. Advantageously, it is believed that the presence of the nitrone and phenolic functionalities allows a regenerative mechanism to take place. Furthermore it has been found that the performance of nitrones that have a phenolic group cannot be achieved by simply adding two different antioxidants, one with a phenolic functionality and another with nitrone functionality. Rather, the presence of both functionalities in the same molecule is an important aspect of their favorable performance.

The cosmetic compositions of the invention are useful for the treatment and protection of skin from free radicals caused, for instance, by exposure to ultraviolet light, such as UVA and UVB rays, as well as other harmful forms of radiation, such as long wave infrared.

Thus, for instance, the cosmetic compositions may be used in a method for inhibiting the degradation of collagen. According to such method, an effective amount of the composition may be topically administering to skin in need of such treatment.

The compositions may also be used in a method for reducing the visible signs of aging, which may result from the radical induced degradation of collagen in the skin, by applying to skin in need of such treatment the composition. Visible signs of aging may include, for instance, development of textural discontinuities such as wrinkles and coarse deep wrinkles, skin lines, crevices, bumps, large pores, or unevenness or roughness, reducing fine lines, loss of skin elasticity (loss and/or inactivation of functional skin elastin), sagging (including puffiness in the eye area and jowls), loss of skin firmness, loss of skin tightness, loss of skin recoil from deformation, discoloration (including undereye circles), blotching, sallowness, hyperpigmented skin regions such as age spots and freckles, keratoses, abnormal differentiation, hyperkeratinization, elastosis, and other histological changes in the stratum corneum, dermis, epidermis, the skin vascular system (e.g., telangiectasia or spider vessels), and underlying tissues, especially those proximate to the skin.

In practicing the methods of the invention, the cosmetic composition are generally administered topically by applying or spreading the compositions onto the skin. A person of ordinary skill in the art can readily determine the frequency with which the cosmetic compositions should be applied. The frequency may depend, for example, on the amount of sunlight that an individual is likely to encounter in a given day and/or the sensitivity of the individual to sunlight. By way of non-limiting example, administration on a frequency of at least once per day may be desirable.

Some embodiments of the invention will now be described in detail in the following Examples.

EXAMPLES

Example 1

Synthesis of (Z)—N-(4-hydroxybenzylidene)-2-methylpropan-2-amine oxide (pHBz-tBHA)

A 100 mL 1-neck flask was equipped with a magnetic stirrer and a rubber septum. The flask was charged with 3.05 grams (0.025 moles) of 4-hydroxybenzaldehyde, 2.23 grams (0.025 moles) of t-butylhydroxylamine crystals, and 25 mL of methanol. The solution was stirred at room temperature over the weekend, during which time the nitrone separated as white crystals. The nitrone was isolated by filtration. It was washed on the filter with a small amount of methanol and was air-dried. The yield of nitrone was 3.92 grams (81%). MP=219-221° C. $^{13}$C-NMR analysis shows peaks at 38.38, 145.73, 143.43, 126.34, 171.82, 133.36, and 81.13 ppm. $^{1}$H-NMR analysis shows peaks at 1.574 ppm (singlet, intensity 9); 7.789 ppm (singlet, intensity 1); 8.219 ppm (doublet, intensity 2); and 6.850 ppm (doublet, intensity 2).

Example 2

(Z)—N-(4-hydroxy-3,5-dimethylbenzylidene)propan-2-amine oxide (DMHBZ-IPHA)

The procedure of example 1 is followed, except 3,4-dimethyl-4-hydroxybenzaldehyde and a 15 wt. % solution of isopropylhydroxylamine in water are used as the starting materials. The yield of nitrone is 81%. MP=201-203° C. $^{13}$C-NMR analysis shows peaks at 30.87, 77.74, 148.12, 132.92, 141.94, 135.49, 26.75, and 167.99 ppm. $^{1}$H-NMR analysis shows peaks at 1.416, 1.449 ppm (doublet, intensity 6); 4.269 ppm (heptet, intensity 1); 7.696 ppm (singlet, intensity 1.5); 7.921 ppm (singlet, intensity 1.5); and 2.237 ppm (singlet, intensity 6).

Example 3

Synthesis of (Z)—N-(4-hydroxy-3-methoxybenzylidene)propan-2-amine oxide (VAN-IPHA)

The procedure of example 1 is followed, except vanillin and isopropylhydroxylamine crystals are used as the starting materials. The yield of nitrone is 81%. MP=178-180° C. Analysis: GC/MS analysis shows m/e peaks at 209 (parent), 193, 178 (base), 167, 151, and 124.

Example 4

Synthesis of (Z)—N-(2-hydroxybenzylidene)propan-2-amine oxide (SAL-IPHA)

The procedure of example 1 is followed, except salicylaldehyde and isopropylhydroxylamine crystals are used as the starting materials. The yield is 97%. MP=36-39° C. Analysis: $^{13}$C-NMR analysis shows peaks at 31.00, 77.35, 150.75, 128.39, 169.86, 129.98, 144.82, 130.38, and 143.47 ppm. $^{1}$H-NMR analysis shows peaks at 1.454, 1.486 ppm (doublet, intensity 6); 4.445 ppm (heptet, intensity 1); 8.094 ppm (singlet, intensity 1); and 6.850-7.455 ppm (multiplet, intensity 4).

Example 5

Synthesis of (Z)—N-(4-hydroxy-3-methoxybenzylidene)-2-methylpropan-2-amine oxide (VAN-tBHA)

The procedure of example 1 is followed, except vanillin and t-butylhydroxyamine crystals are used as the starting materials. The yield of nitrone is 81%. MP=198-200° C.

Analysis: $^{13}$C-NMR analysis shows peaks at 38.38, 81.24, 145.9, 136.5, 123.8, 161.2, 158.5, 126.2, 133.8, and 66.4 ppm. $^1$H-NMR analysis shows peaks at 1.583 ppm (singlet, intensity 9); 8.321, 8.330 ppm (doublet, intensity 1); 7.805 ppm (singlet, intensity 1); 6.842, 6.884 ppm (doublet, intensity 1); 7.585, 7.629 ppm (doublet, intensity 1); and 3.905 ppm (singlet, intensity 3).

Example 6

Synthesis of (Z)—N-(4-hydroxybenzylidene)propan-2-amine oxide (pHBz-IPHA)

The procedure of example 1 is followed, except p-hydroxybenzaldehyde and isopropylhydroxylamine crystals are used as the starting materials. The yield of nitrone is 84%. MP=217-218° C. GC/MS analysis shows m/e peaks at 179 (parent), 163, 148 (base), 137, 121, and 94.

Example 7

Synthesis of sodium (Z)-2-hydroxy-5-((isopropyloxidoimino)methyl)benzoate (FSANa-IPHA)

The procedure of example 1 is followed, except 5-formylsalicylic acid (FSA) and isopropylhydroxylamine crystals are used as starting materials. The reaction mixture is stirred at room temperature overnight, then one equivalent of sodium hydroxide (based on FSA) is added as a 20 wt. % solution in water. This mixture is again stirred at room temperature overnight, then the nitrone is isolated by removing the solvents under vacuum. The yield of the nitrone sodium salt is 96%. MP=230-233° C., accompanied by evolution of gas. $^{13}$C-NMR analysis shows peaks at 10.89, 57.96, 126.05, 124.87, 108.26, 129.75, 111.73, 154.38, 109.60, and 165.70 ppm. $^1$H-NMR analysis shows peaks at 1.434 ppm (doublet, intensity 6); 4.319 ppm (heptet, intensity 1); 8.552 ppm (singlet) and 8.348 ppm (doublet) (combined intensity 2); 6.959 ppm (doublet, intensity 1); and 7.891 ppm (singlet, intensity 1).

Example 8

Synthesis of (Z)—N-(2,4-dihydroxybenzylidene)propan-2-amine oxide (DHBz-IPHA)

The procedure of example 1 is followed, except 2,4-dihydroxybenzaldehyde and IPHA crystals are used as starting materials. The yield of nitrone is 63%. MP=155-157° C. $^{13}$C-NMR analysis shows peaks at 20.32, 63.83, 134.39, 138.72, 108.95, 104.31, 162.83, 107.31, and 161.17 ppm. $^1$H-NMR analysis shows peaks at 1.341 ppm (doublet, intensity 6); 4.342 ppm (quintet, intensity 1); 7.963 ppm (singlet, intensity 1); 7.124 ppm (doublet, intensity 1); 6.143-6.305 ppm (doublet of doublets, intensity 1); 6.138 ppm (doublet, intensity 1); and 10.018, 13.778 ppm (singlet, intensity 1).

Example 9

Synthesis of Sodium (Z)—N-(4-hydroxy-2-oxobenzylidene)propan-2-amine oxide (DHBzNa-IPHA)

This material is made by the reaction of one equivalent of (Z)—N-(2,4-dihydroxybenzylidene)propan-2-amine oxide (DHBz-IPHA) from Example 8 with one equivalent of sodium hydroxide in water. The mixture is warmed to dissolve all of the solids, then it is stirred at room temperature overnight. The nitrone is isolated by removing the water under vacuum. The yield of the nitrone sodium salt is quantitative. MP=>300° C. $^{13}$C-NMR analysis shows peaks at 22.59, 67.54, 143.87, 137.83, 137.72, 104.31, 162.83, 107.31, and 161.17 ppm. $^1$H-NMR analysis shows peaks at 1.415 ppm (doublet, intensity 6); 4.274 ppm (heptet, intensity 1); 7.848 ppm (singlet, intensity 1); 7.481 ppm (doublet, intensity 1); 6.213-6.267 ppm (doublet of doublets, intensity 1); and 6.086 ppm (doublet, intensity 1).

Example 10

Antioxidant Potential

Antioxidant potential is evaluated using the Oxygen Radical Absorbance Capacity (ORAC) protocol. ORAC is a chemical in-vitro method based on the hydrogen atom transfer (HAT) mechanism. ORAC measures antioxidant inhibition of peroxyl radical induced oxidations and thus reflects classical radical chain breaking antioxidant activity by H atom transfer. In this assay, the peroxyl radical reacts with a fluorescent probe to form a non-fluorescent product. This is quantitated using a fluorescence measurement. Antioxidant capacity is determined by decreased rate and amount of product formed over time. This assay depends upon the free radical damage to the fluorescent probe resulting in the change in its fluorescence intensity. The change of fluorescence intensity is an indicator of the degree of free radical damage. In the presence of an antioxidant, the inhibition of free radical damage is reflected in higher fluorescence intensity and can be measured as antioxidant capacity against the free radicals. The uniqueness of ORAC assay is that the reaction is driven to completion. This allows calculation of the area under the curve (AUC) and gives an absolute quantitation of antioxidancy as opposed to relative measurements in many other assays.

As noted, the longer it takes to observe a decrease in fluorescence, the higher the antioxidant (AO) potential. From the AUC for a given antioxidant, the AUC for blank is subtracted to give its ORAC value. The concentration of AO needed to give the same AUC values as Trolox is calculated and used to represent the Trolox equivalent AO Capacity (TEAC). Trolox is ((±)-6-Hydroxy-2,5,7,8-tetramethylchromane-2-carboxylic acid, CAS #53188-07-1), and is used as an internal control.

The ORAC test is conducted in the compounds of Examples 1-5 (inventive compounds) as well as to Vitamin C, Vitamin E, and the following comparative compounds:

The TEAC values calculated from the ORAC values are listed the Table 2.

| AO | TEAC |
|---|---|
| Vitamin C (comparative) | 0.76 |
| Vitamin E (comparative) | 0.13 |
| SAL-IPHA (inventive) | 3.02 |
| pHBz-IPHA (inventive) | 8.67 |
| DMHBz-IPHA (inventive) | 1.56 |
| VAN-IPHA (inventive) | 5.41 |
| VAN-tBHA (inventive) | 4.42 |
| PBN (comparative) | 0.04 |
| BHT (comparative) | 0.11-0.21 |
| PBN + BHT (comparative) | 0.24 |
| VAL-IPHA (comparative) | 0.18 |

Surprisingly, it is found that the compounds of the invention displayed significantly higher ORAC values compared to the known antioxidants Vitamin E or C. It is also evident that the TEAC values of phenolic AOs such as BHT, a non-aromatic nitrone such as VAL-IPHA, or an aromatic nitrone such as PBN are not very high compared to the TEAC values of the compounds of the invention, which contain both phenolic and nitrone moieties. The TEAC value for a physical blend of an aromatic nitrone and a phenolic AO (PBN+BHT) is relatively small also. This leads us to believe that for the regenerative mechanism to take place, the nitrone and the phenolic functionalities need to be part of the same molecule.

In the following Examples, inventive compounds VAN-IPHA (Example 3) and pHBz-IPHA (Example 6) are tested for efficacy in preventing collagen degradation and compared to the Vitamin E. In the figures, VAN-IPHA is labeled as "VAN" and pHBz-IPHA is labeled as pHBz.

Example 11

Inhibition of Collagen Degradation

Figure 1:
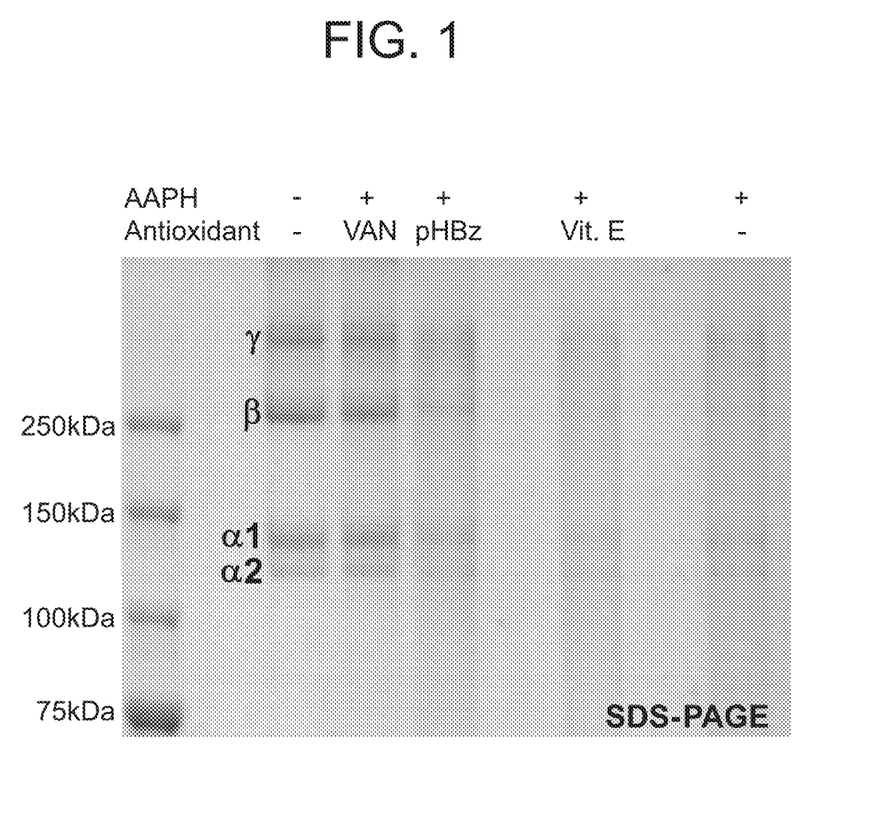
FIG. 1 shows a SDS-PAGE analysis of collagen upon AAPH treatment in the presence of inventive and comparative antioxidant compounds and buffer solution.

Type I collagen, typically found in abundance in skin, is dissolved in 0.04 M acetic acid, pH 4.3, prior to different treatments. For radical induced collagen degradation, aqueous radical initiator 2,2'-azobis-2-methyl-propanimidamide dihydrochloride (AAPH) is used. The collagen samples are incubated with AAPH in the presence of VAN-IPHA (Example 3), pHBz-IPHA (Example 6), and vitamin E (comparative) of the same concentration to determine the efficacy of these antioxidants in preventing collagen degradation. After incubation at 50° C. for 90 mins, the collagen samples are analyzed by SDS-PAGE to determine the degree of degradation by the remaining amount of γ-chain, which is a covalently cross-linked trimer for collagen. As shown in FIG. 1, the extent of collagen degradation is significantly less in the presence of VAN-IPHA compared to pHBz-IPHA, vitamin E, or control solution in which no antioxidant was present.

Figure 2:
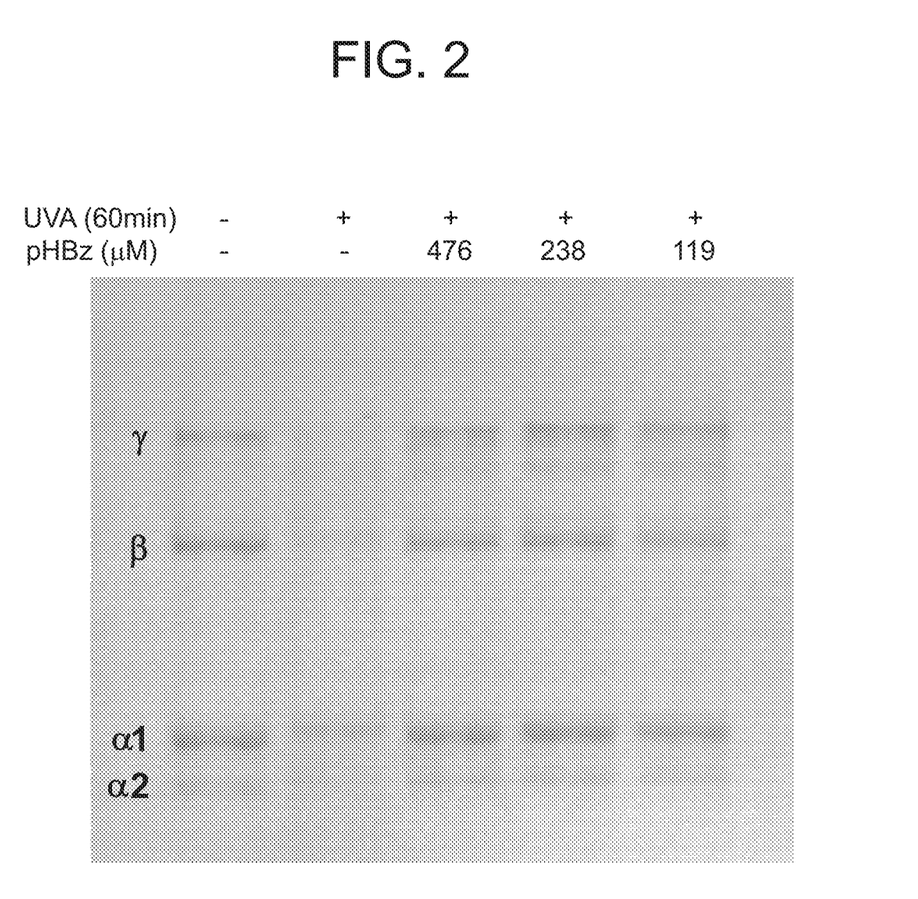
FIG. 2 shows a SDS-PAGE analysis of collagen in the absence and presence of different concentrations of an inventive antioxidant compound after exposure to UVA irradiation for 60 min.

In addition to the oxidative stress due to radical and ROS generation, oxidative damage to collagen can also be induced by UVA irradiation. Similar to the radical-induced collagen degradation, the effect of UVA in collagen degradation is mitigated by the presence of nitrones. FIG. 2 shows the SDS-PAGE analysis of the effect of pHBz-IPHA at various concentrations in preventing UVA-induced collagen damage.

Figure 3:
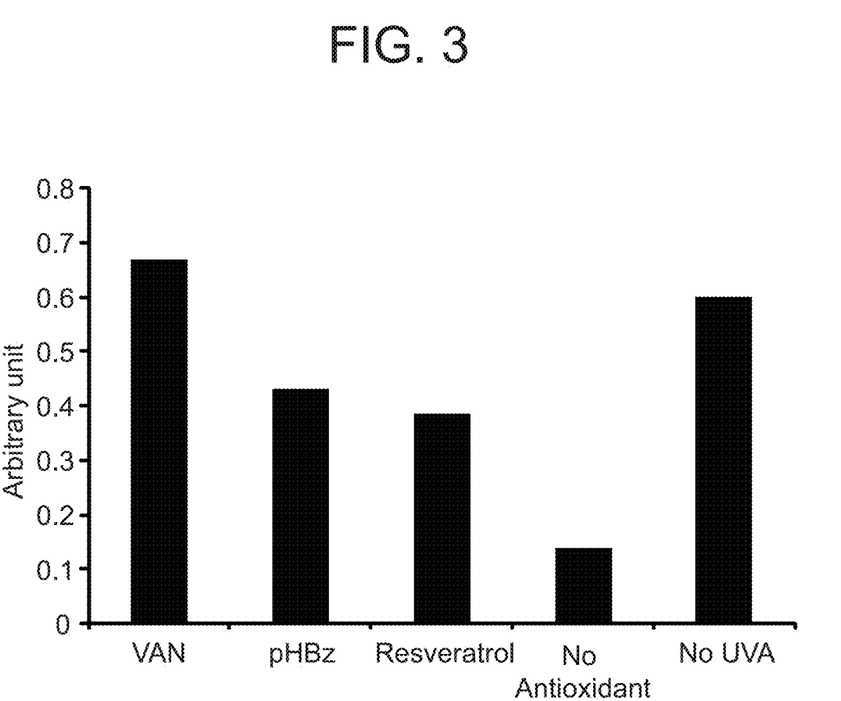
FIG. 3 is a densitometry plot of collagen γ-bands on SDS-PAGE of samples containing antioxidant at concentration of 238 μM. The plot shows the effects of antioxidants on UVA-induced collagen degradation.

Similar to the prevention of radical-induced degradation, better efficacy in the inhibitory effect of preventing UVA-induced degradation is also observed for VAN-IPHA (FIG. 3). In this analysis, the effects of VAN-IPHA and pHBz-IPHA are compared to a highly efficacious antioxidant, Resveratrol. Due to the known photostability issue of Resveratrol, its effect in preventing UVA-induced collagen degradation is similar to pHBz-IPHA, while VAN-IPHA shows better efficacy than Resveratrol. The stability of nitrones of the invention provide an advantageous alternative solution for antioxidant needs in cosmetic applications, such as anti-aging.

What is claimed is:

1. A method for inhibiting the degradation of collagen in skin, the method comprising: topically administering to the skin an effective amount of a composition comprising:
  (a) an antioxidant compound selected from the group consisting of (Z)—N-(2-hydroxybenzylidene)propan-2-amide oxide, (Z)—N-(4-hydroxybenzylidene)propan-2-amine oxide, (Z)—N-(4-hydroxy-3-methoxybenzylidene)propan-2-amine oxide, (Z)—N-(4-hydroxy-3-methoxybenzylidene)-2-methylpropan-2-amine oxide, and mixtures thereof; and
  (b) a dermatologically acceptable carrier.

2. The method of claim 1, wherein the compound of formula I is (Z)—N-(4-hydroxy-3-methoxybenzylidene)propan-2-amine oxide or (Z)—N-(4-hydroxybenzylidene)propan-2-amine oxide.

3. A method for reducing the visible signs of aging, the method comprising: applying to skin in need of such treatment a composition comprising:

(a) an antioxidant compound selected from the group consisting of (Z)—N-(2-hydroxybenzylidene)propan-2-amide oxide, (Z)—N-(4-hydroxybenzylidene)propan-2-amine oxide, (Z)—N-(4-hydroxy-3-methoxybenzylidene)propan-2-amine oxide, (Z)—N-(4-hydroxy-3-methoxybenzylidene)-2-methylpropan-2-amine oxide, and mixtures thereof; and (b) a dermatologically acceptable carrier.

4. The method of claim 3, wherein the compound of formula I is (Z)—N-(4-hydroxy-3-methoxybenzylidene) propan-2-amine oxide or (Z)—N-(4-hydroxybenzylidene) propan-2-amine oxide.

\* \* \* \* \*